US006911331B2

(12) United States Patent
Famodu et al.

(10) Patent No.: US 6,911,331 B2
(45) Date of Patent: Jun. 28, 2005

(54) CHORISMATE BIOSYNTHESIS ENZYMES

(75) Inventors: Omolayo O. Famodu, Newark, DE (US); William D. Hitz, Wilmington, DE (US); Jonathan E. Lightner, Mulino, OR (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 27 days.

(21) Appl. No.: 10/105,729

(22) Filed: Mar. 22, 2002

(65) Prior Publication Data

US 2003/0003557 A1 Jan. 2, 2003

Related U.S. Application Data

(63) Continuation-in-part of application No. 09/743,210, filed on Feb. 23, 2001, now abandoned.
(60) Provisional application No. PCT/US99/16352, filed on Jul. 20, 1999, and provisional application No. 60/093,611, filed on Jul. 21, 1998.

(51) Int. Cl.$^7$ .......................... C12P 21/06; C12N 9/00; C12N 1/20; C12N 15/00; C07H 21/04
(52) U.S. Cl. ..................... 435/193; 435/4; 435/6; 435/69.1; 435/183; 435/252.3; 435/320.1; 536/23.2; 536/23.6
(58) Field of Search ................. 435/4, 6, 69.1, 435/183, 193, 252.3, 320.1; 536/23.2, 23.6

(56) References Cited

U.S. PATENT DOCUMENTS 5,187,071 A  2/1993  Fischer et al.

FOREIGN PATENT DOCUMENTS

| EP | 0 608 722 A1 | 8/1994 |
| EP | 0 832 978 A2 | 4/1998 |
| WO | WO 95/33843 | 12/1995 |
| WO | WO 97/26366 | 7/1997 |
| WO | WO 98/03661 | 1/1998 |

OTHER PUBLICATIONS

Dyer et al. Accession A35016. Jul. 20, 1990.*
Attwood et al. Which craft is best in bioinformatics? Comput. Chem. 2001, vol. 25(4), pp. 329–339.*
Ponting, C.P. Issues in predicting protein function from sequence. Brief. Bioinform. Mar. 2001, vol. 2(1), pp. 19–29.*
EMBL Database Accession No. Y14797.1, Wind, J.C. et al., Jan. 1, 1998, Three differentially expressed 3–deoxy–D–arabino–heptulosonate 7–phosphate synthase genes in *Morinda citrifolia*, XP–002129965.
EMBL Database Accession No. AF012864, Batz, O. et al., 09–11–197, Extensive reprogramming of cellular metabolism by fungal elicitor of infection in parsley suggests a new perception of defense–related genes, XP–002129966.
William E. Dyer et al., Journ. of Biol Chem., vol. 265 1608–1614, 1990, A cDNA Encoding 3–Deoxy–D–arabino–heptulosonate 7–Phosphate Synthase from *Solanum tuberosum* L., XP–002129967.
Jorn Gorlach et al., Plant Mol. Biol., vol. 23:697–706, 1993, Differential expression of tomato (*Lycopersicon esculentum* L.) genes encoding shikimate pathway isoenzymes. I. 3–Deoxy–D–arabino–heptulosonate 7–phosphate synthase, XP–002121067.
James D. Jones et al., Plant Physiol., vol. 108(4):1413–1421, 1995, Impaired Wound Induction of 3–Deoxy–D–arabino–heptulosonate–7–phosphate (DAHP) Synthase and Altered Stem Development in Transgenic Potato Plants Expressing a DAHP Synthase Antisense Construct, XP–002121068.
Klaus M. Herrmann, Plant Physiol., vol. 107:Jul. 12, 1995. The shikimate Pathway as an Entry to Aromatic Secondary Metabolism, XP–002121069.
EMBL Database Accession No.: AI677182, May 25, 1999, Walbot, V., Maize ESTs from various cDNA libraries sequenced at Stanford University, XP–002121070.
EMBL Database Accession No.: AI615213, Apr. 26, 1999, Walbot, V., Maize ESTs from various cDNA libraries sequenced at Stanford University, XP–002129968.
EMBL Database Accession No.: AI443687, Mar. 16,1999, Shoemaker, R. et al., Public Soybean EST Project, XP–002129969.
EMBL Database Accession No.: AU068686, Jun. 7, 1999, Sasaki, T. et al., XP–002129970.
Yunxia Wang et al., Plant Physiol, vol. 97:847–848, 1991, Cloning and Nucleotide Sequence of a Complementary DNA Encoding 3–Deoxy–D–arabino–Heptulosonate 7–Phosphate Synthase from Tobacco.
Brian Keith et al., PNAS, vol. 88:8821–8825, Oct. 1991, Differential induction of 3–deoxy–D–arabino–heptulosonate 7–phosphate synthase genes in *Arabidopsis thaliana* by wounding and pathogenic attack.
Jianmin Zhao et al., Plant Phys., vol. 100:1075–1076, 1992, Cloning and Sequencing of a Second cDNA Encoding 3–Deoxy–D–arabino–Heptulosonate 7–Phosphate Synthase from *Solanum tuberosum* L.
National Center for Biotechnology Information General Identifier No. 2398679, Sep. 12, 1997, Wind, J.C. et al., Three differentially expressed 3–deoxy–D–arabino–heptulosonate 7–phsophate synthase genes in *Morinda citrifolia*.
National Center for Biotechnology Information General Identifier No. 2546988, Wind, J.C. et al., Three differentially expressed 3–deoxy–D–arabino–heptulosonate 7–phsophate synthase genes in *Morinda citrifolia*.

(Continued)

Primary Examiner—Manjunath N. Rao
Assistant Examiner—Christian L Fronda

(57) ABSTRACT

This invention relates to an isolated nucleic acid fragment encoding a DAHP synthetase. The invention also relates to the construction of a chimeric gene encoding all or a portion of the DAHP synthetase, in sense or antisense orientation, wherein expression of the chimeric gene results in production of altered levels of the DAHP synthetase in a transformed host cell.

7 Claims, No Drawings

OTHER PUBLICATIONS

National Center for Biotechnology Information General Identifier No. 584777, Dyer, W.E. et al., A cDNa encoding 3–deoxy–D–arabino–heptulosonate 7–phosphate synthase from *Solanum tuberosum* L.

National Center for Biotechnology Information General Identifier No. 114193, May 30, 2000, Wang, Y. et al., Cloning and nucleotide sequence of a complementary DNA encoding 3–deoxy–D–arabino–heptulosonate 7–phosphate synthase from tobacco.

Gloria K. Muday et al., Plant Phys., vol. 98:496–500, 1992, Wounding Induces One of Two isoenzymes of 3–Deoxy–D–arabino–Heptulosonate 7–Phosphate Synthase in *Solanum tuberosum* L.

Robert J. Ganson et al., Plant Phys., vol. 82:203–210, 1986, The Two–isozyme System of 3–Deoxy–D–arabino–Heptulosonate 7–Phosphate Synthase in *Nicotiana silvestris* and Other Higher Plants.

P.R. Srinivasan et al., J. Biol. Chem., vol. 234:716–722, 1959, 2–Keto–3–deoxy–D–arabo–heptonic Acid 7, Phosphate Synthetase.

EMBL Sequence Library Data Accession No.: AI731017, Jun. 12, 1999, Blewitt, M. et al., ESTs from Developing Cotton Fiber.

EMBL Sequence Library Data Accession No. AI728073, Jun. 12, 1999, Blewitt, M. et al., ESTs from Developing Cotton Fiber.

EMBL Sequence Library Data Accession No.: AI489566, Mar. 17, 1999, Alcala, J. et al., Generation of STSs from Tomato Carpel Tissue.

Stephen Bornemann et al., Journ. of Biol. Chem., vol. 270(39):22811–22815, 1995, *Escherichia coli* Chorismate Synthase Catalyzes the Conversion of (6S)–6–Fluoro–5Oenolypyruvylshikimate–3–phosphate to 6–Fluorochorismate.

EMBL Sequence Library Data Accession No.: C72774, Sep. 19, 1997, Sasaki, T. et al., Rice cDNA from Panicle at Flowering stage.

EMBL Sequence Library Data Accession No.: AA750226, Jan. 21, 1998, Nahm, B. H. et al., Large–scale Sequencing Analysis of STSs from Rice Immature Seed.

Andreas Schaller et al., Journ. of Biol. Chem., vol. 256(32):21434–21438, 1991, Molecular Cloning and Analysis of cDNA Coding for Chorismate Synthase from the Higher Plant *Corydalis sempervirens* Pers.

Jorn Gorlach et al., Plant Mol. Biol., vol. 23:707–716, 1993, Differential expression of tomoato (*Lcopersicon esculentum* L.) genes encoding shikimate pathway isoenzymes. II. Chorismate synthase.

Genbank Accession No.: L33595, Jul. 11, 1994, Lim, C.O. et al., Expressed sequence tags of Chinese cabbage flower bud cDNA.

Genbank Accession No.: AA586083, Sep. 11, 1997, Newman, T. et al., Genes galore: a summary of methods for accessing results from large–scale partial sequencing of annoymous Arabidopsis cDNa clones.

EMBL Sequence Library Data Accession No.: AA586083, Sep. 13, 1997, Newman, T. et al., Genes galore: a summary of methods for accessing results from large–scale partial sequencing of anonymous Arabidopsis cDNa clones.

Gary Millar et al., FEBS Letters, vol. 200(1):Nov. 17, 1986, The complete amino acid sequence of 3–dehydroquinate synthase of *Escherichia coli* K–12.

National Center for Biotechnology Information General Identifier No. 114181, May 30, 2000, Millar, G. et al., The complete amino acid sequence of 3–dehydroquinate synthase of *Escherichia coli* K–12.

EMBL Sequence Library Data Accession No.: P34002, Feb. 1, 1994, Martin, P. R. et al., Characterization of pilQ, a nw gene required for the biogenesis of type 4 fimbriae in *Pseudomonas aeruginosa*.

Nicholas Nikolaides et al., Tetrahedron Letters, vol. 30(12):1461–1464, 1989, Design and Synthesis of Substrate Analogs for the Inhibition of Dehydrogquinate Synthase.

John W. Frost et al., Biochemistry, vol. 23:4470–4475, 1984, Dehydroquinate Synthase from *Escherichia coli*: Purification, Cloning, and Construction of Overproducers of the Enzyme.

D. L. Pomplianao et al., J. Am. Chem. Soc., vol. 111:1866–1871, 1989, Probing Lethal Metabolic Pekturbations in Plants with Chemical Inhibition of Dehdyroquinate Synthase.

Genbank Accession No.: AI065473, Jul. 24, 1998, Schutz, K. et al., Expressed sequence tags from *Z. mays*.

EMBL. Sequence Library Data Accession No.: AI065473, Jul. 27, 1998, Schutz, K. et al., Expressed sequence tags from *Z. mays*.

EMBL Sequence Library Data Accession No.: AI637200, Apr. 27, 1999, Walbot, V., Maize ESTs from various cDNA libraries sequenced at Stanford University.

EMBL Sequence Library Data Accession No.: AU56551, Sasaki, T. et al., Rice cDNA from mature leaf.

Markus Bischoff et al., Plant Mol. Biol., vol. 31:69–76, 1996, Cloning of a cDNA encoding a 3–dehydrogquinate synthase from a higher plant, and analysis of the organ–specific and elicitor–induced expression of the corresponding gene.

Craig M. Stephens et al., Essential Cysteines in 3–Deoxy–D–arabino–heptulosonate–7–phosphate Synthase from *Escherichia coli*, J. Biol. Chem., Mar. 25, 1992, vol. 267, No. 9, pp. 5762–5767.

Prem S. Subramaniam et al., Substrate Ambiguity of 3–Deoxy–D–manno–Octulosonate 8–Phosphate Synthase from *Neisseria gonorrhoeae* in the Context of its Membership in a Protein Family Containing a Subset of 3–Deoxy–D–arabino–Heptulosonate 7–Phosphate Synthases, J. Bacteriol., Jan. 1998, vol. 180, No. 1, pp. 119–127.

* cited by examiner

CHORISMATE BIOSYNTHESIS ENZYMES

This application is a continuation-in-part application of U.S. application Ser. No. 09/743,210, filed Feb. 23, 2001, now abandoned, which was the National Stage of International Application No. PCT/US99/16352, filed Jul. 20, 1999, which claims the benefit of U.S. Provisional Application No. 60/093,611, filed Jul. 21, 1998.

FIELD OF THE INVENTION

This invention is in the field of plant molecular biology. More specifically, this invention pertains to nucleic acid fragments encoding enzymes involved in chorismate biosynthesis in plants and seeds.

BACKGROUND OF THE INVENTION

Chorismate biosynthesis involves the last few steps in the common pathway for the production of the aromatic amino acids phenylalanine, tyrosine and tryptophan. The first step in chorismate biosyntheis is performed by 3-deoxy-D-arabino-heptulosonate 7-phosphate synthase, also called DAHP synthetase. Two differentially expressed forms of this enzyme are present in plant tissues and are important regulators of the flux to aromatic amino acid biosynthesis. DAHP synthetase has been described for tomato, tobacco, potato, alfalfa and *Arabidopsis thaliana* (Wang, Y., et al. (1991) *Plant Physiol.* 97:847–848; Gorlach, J., et al. (1993) *Plant Mol Biol* 23:697–706; Dyer, et al. (1990) *J. Biol. Chem.* 265:1608–1614; Keith, B., et al. (1991) *Proc. Natl. Acad. Sci. USA* 88:8821–8825; Zhao, J., and Herrmann, K. M. (1993) *Plant Physiol.* 100:1075–1076).

Manipulating either the amount or activity of these enzymes would afford manipulation of the ratio of aromatic to non-aromatic amino acids in plants, including corn, rice, sorghum, soybean and wheat. This enzyme should also be useful for high throughput screening of compounds suitable for use as herbicides.

SUMMARY OF THE INVENTION

The instant invention relates to isolated nucleic acid fragments encoding DAHP synthetases. Specifically, this invention concerns an isolated nucleic acid fragment encoding a DAHP synthetase and an isolated nucleic acid fragment that is substantially similar to an isolated nucleic acid fragment encoding a DAHP synthetase. In addition, this invention relates to a nucleic acid fragment that is complementary to the nucleic acid fragment encoding DAHP synthetase.

An additional embodiment of the instant invention pertains to a polypeptide encoding all or a substantial portion of a DAHP synthetase.

In another embodiment, the instant invention relates to a chimeric gene encoding a DAHP synthetase, or to a chimeric gene that comprises a nucleic acid fragment that is complementary to a nucleic acid fragment encoding a DAHP synthetase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a DAHP synthetase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a DAHP synthetase in a transformed host cell comprising: a) transforming a host cell with a chimeric gene comprising a nucleic acid fragment encoding a DAHP synthetase; and b) growing the transformed host cell under conditions that are suitable for expression of the chimeric gene wherein expression of the chimeric gene results in production of altered levels of DAHP synthetase in the transformed host cell.

An addition embodiment of the instant invention concerns a method for obtaining a nucleic acid fragment encoding all or a substantial portion of an amino acid sequence encoding a DAHP synthetase.

A further embodiment of the instant invention is a method for evaluating at least one compound for its ability to inhibit the activity of a DAHP synthetase, the method comprising the steps of: (a) transforming a host cell with a chimeric gene comprising a nucleic acid fragment encoding a DAHP synthetase, operably linked to suitable regulatory sequences; (b) growing the transformed host cell under conditions that are suitable for expression of the chimeric gene wherein expression of the chimeric gene results in production of DAHP synthetase in the transformed host cell; (c) optionally purifying the DAHP synthetase expressed by the transformed host cell; (d) treating the DAHP synthetase with a compound to be tested; and (e) comparing the activity of the DAHP synthetase that has been treated with a test compound to the activity of an untreated DAHP synthetase, thereby selecting compounds with potential for inhibitory activity.

BRIEF DESCRIPTION OF THE SEQUENCE LISTINGS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

| | DAHP Synthetases | | |
|---|---|---|---|
| | | SEQ ID NO: | |
| Plant | Clone Designation | (Nucleotide) | (Amino Acid) |
| Corn | cr1n.pk0042.f4 | 1 | 2 |
| Rice | rls24.pk0031.d1-3' | 3 | 4 |
| Rice | rls24.pk0031.d1-5' | 5 | 6 |
| Soybean | sfl1.pk0089.a8 | 7 | 8 |
| Wheat | wl1n.pk0095.a10 | 9 | 10 |

The Sequence Listing contains the one letter code for nucleotide sequence characters and the three letter codes for amino acids as defined in conformity with the IUPAC- IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA—DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 80% identical, preferably at least about 85% identical, to the amino acid sequences reported herein. Preferred are those nucleic acid fragments whose nucleotide sequences encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence often or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several DAHP synthetases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other DAHP synthetases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the ratio of aromatic to non-aromatic amino acids in those cells. This may also create plants that are resistant to herbicides.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptide to different cellular compartments, or to facilitate its secretion from the cell. It is thus envisioned that the chimeric gene described above may be further supplemented by altering the coding sequence to encode the instant polypeptide with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptide (or portions thereof) may be produced in heterologous host cells, particularly in the cells of microbial hosts, and can be used to prepare antibodies to the these proteins by methods well known to those skilled in the art. The antibodies are useful for detecting the polypeptide of the instant invention in situ in cells or in vitro in cell extracts. Preferred heterologous host cells for production of the instant polypeptide are microbial hosts. Microbial expression systems and expression vectors containing regulatory sequences that direct high level expression of foreign proteins are well known to those skilled in the art. Any of these could be used to construct a chimeric gene for production of the instant polypeptide. This chimeric gene could then be introduced into appropriate microorganisms via transformation to provide high level expression of the encoded DAHP synthetase. An example of a vector for high level expression of the instant polypeptide in a bacterial host is provided (Example 6).

Additionally, the instant polypeptide can be used as a target to facilitate design and/or identification of inhibitors of those enzymes that may be useful as herbicides. This is desirable because the polypeptide described herein catalyzes the first committed step in aromatic amino acid biosynthesis through the shikimate pathway. Accordingly, inhibition of the activity of the enzyme described herein could lead to inhibition plant growth. Thus, the instant polypeptide could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptide disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---------|--------|-------|
| cr1n | Corn Root From 7 Day Old Seedlings* | cr1n.pk0042.f4 |
| rls24 | Rice Leaf 15 Days After Germination, 24 Hours After Infection of Strain *Magaporthe grisea* 4360-R-67 (AVR2-YAMO); Susceptible | rls24.pk0031.d1-3' |
| sfl1 | Soybean Immature Flower | sfl1.pk0089.a8 |
| wl1n | Wheat Leaf From 7 Day Old Seedling* | wl1n.pk0095.a10 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding DAHP synthetases were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding DAHP Synthetase

The BLASTX search using the EST sequences from clones listed in Table 3 revealed similarity of the polypeptides encoded by the cDNAs to DAHP synthetases from *Morinda citrifolia* (NCBI General Identifier No. 2398679 and 2546988), *Solanum tuberosum* (NCBI General Identifier No. 584777), or *Nicotiana tabacum* (NCBI General Identifier No. 114193). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to DAHP Synthetases

| Clone | Status | NCBI General Identifier No. | BLAST pLog Score |
|---|---|---|---|
| cr1n.pk0042.f4:fis | FIS | 2398679 | 254.00 |
| rls24.pk0031.d1-3' | EST | 584777 | 33.15 |
| rls24.pk0031.d1-5' | EST | 2546988 | 72.15 |
| sfl1.pk0089.a8 | FIS | 114193 | 254.00 |
| wl1n.pk0095.a10 | FIS | 2398679 | 134.00 |

The data in Table 4 represents a calculation of the percent identity of the amino acid sequences set forth in SEQ ID NOs:2, 4, 6, 8 and 10 and the *Morinda citrifolia* (NCBI General Identifier No. 2398679) sequence.

TABLE 4

Percent Identity of Amino Acid Sequences Deduced From the Nucleotide Sequences of cDNA Clones Encoding Polypeptides Homologous to DAHP Synthetases

| SEQ ID NO. | Percent Identity to 2398679 |
|---|---|
| 2 | 81.4 |
| 4 | 75.3 |
| 6 | 51.9 |
| 8 | 80.2 |
| 10 | 84.6 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode entire corn and soybean DAHP synthetases, a substantial portion of a wheat DAHP synthetase, and two portions of a rice DAHP synthetase. These sequences represent the first corn, rice, soybean and wheat sequences encoding DAHP synthetase. The nucleotide sequence of SEQ ID NO:1 includes an open reading frame including a start codon (positions 86–88) and stop codon (positions 1699–1701) that encodes the amino acid sequence of SEQ ID NO:2. The nucleotide sequence of SEQ ID NO:7 includes an open reading frame including a start codon (positions 43–46) and stop codon (positions 1639–1641) that encodes the amino acid sequence of SEQ ID NO:2.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR)

of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL2 1 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of DAHP Synthetases The polypeptides described herein may be produced using any number of methods known to those skilled in the art.

Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for DAHP synthetase are presented by Muday and Herrmann (1992) *Plant Physiol.* 98: 496–500, Ganson et al. (1986) *Plant Physiol.* 82: 203–210, and Srinivason and Sprinson (1959) *J. Biol. Chem.* 234: 716–722.

SEQUENCE LISTING

```
<160> NUMBER OF SEQ ID NOS: 10

<210> SEQ ID NO 1
<211> LENGTH: 2003
<212> TYPE: DNA
<213> ORGANISM: Zea mays

<400> SEQUENCE: 1
gcacgagctc agcactgcac gactcctccc ccatctacca ctacctgtct acctacccag      60
cccatcgatc acccctcgca acgcaatggc gctggccacc aactccgccg ctgccgcagc     120
agctgccgta tccggcggcg cggcatccca gccgcaccgc gcggccacgt tcctcccgct     180
gaagaggcgc accatctccg ccatccacgc cgccgacccg tctaagaaca acgggcccgc     240
cgtccccgcg gccgccgccg ctaagtcatc tgcctctgcg gtggccacgc cggagaagaa     300
tccggcggcg ccggtaaagt gggcggtcga cagctggaag tcgaagaagg cgctgcagct     360
cccagagtac ccgaaccagg aggagctgga cacggtgctc aaaaccatcg agacgttccc     420
gccggtggtg ttcgccggag aggcgcgcca cctcgaggag cgcatggccg aggccgccat     480
gggccgcgcc ttcatcctcc agggcggcga ctgcgccgag agcttcaagg agttccacgc     540
caacaacatc cgtgacacct tccgtatcct gctgcagatg ggcgccgtgc tcatgttcgg     600
tggtcaggtg ccggtcgtca aggtggggag gatggctggc cagtttgcca agccaaggtc     660
cgaaccgttg gaggagaggg acggcgtcaa gctgccaagc tacaggggcg acaacgtcaa     720
cggcgacgac ttcaccgaga agagccgcgt gccagacccg cagaggatga tccgcgccta     780
ctcgcagtcg gtggcgacgc tcaacctgct ccgcgcgttg gcgaccggag ggtacgctgc     840
```

-continued

```
catgcagcgc gtcacacagt ggaacctcga tttcatggat cacagcgagc aaggtgatag      900
gtaccgtgaa ttgggccata gggtggatga ggctcttggg ttcatgactg cagcagggct      960
tacagttgac cacccgataa tgacgactac tgacttctgg acctcacacg agtgccttct     1020
cttaccctac gagcagtctc ttacccgtaa agactccacc agtggccttt tctacgattg     1080
ttcggcccac atgctgtggt ttggtgagcg cactcgtcaa ctcgatggag cgcatgttga     1140
atcccttcgt ggtgttcaca atcctcttgg cataaaggtg agcgacaaaa tgaaccccag     1200
tgacttggtg aagctgattg agattctgaa cccttcaaac aaacctggaa ggatcaccat     1260
aattacaagg atgggggcag agaacatgag agtgaagttg cctcatctca tccgtgctgt     1320
tcgcaatgct ggattaattg tcacatggat tactgatcct atgcatggaa acaccatcaa     1380
ggccccttgt ggcctgaaga ctcgtccatt cgactcaatt ctggctgaag tgcgcgcatt     1440
cttcgacgtg catgatcaag aaggaagtca cccaggaggc atccaccttg aaatgactgg     1500
gcagaacgtg accgagtgca ttggtggatc acggactgtg accttcgatg accttagtga     1560
ccgctaccac acccactgtg acccaaggct gaacgcctcc cagtccctgg agctcgcctt     1620
catcattgca gagaggctca ggaagaggag gatgcggtcg gggctcaaca acagcctgcc     1680
tctgccacca ctggctttct aagtagccga agctgaacag agaaggtaga ggggatagtt     1740
gcggcgactc gaaagattac gcctgtttat ttgttgatgc ttggtgtgga ggcctggtgg     1800
gtgctcttgg cacaagttac atgctgggga gctatacgag ggtacctgtt gcgttgtgga     1860
agacagtagc tagtattatg tgttgtaatt gtatcccttc gtttcatgtt ctgggtgcgt     1920
gacttgtcga ctttgctgct tctggggttc tgaccttggt aaggagagaa taaagagata     1980
atatgagtgc gagatgcttg ctg                                             2003
```

<210> SEQ ID NO 2
<211> LENGTH: 538
<212> TYPE: PRT
<213> ORGANISM: Zea mays

<400> SEQUENCE: 2

```
Met Ala Leu Ala Thr Asn Ser Ala Ala Ala Ala Ala Ala Ala Val Ser
1               5                  10                  15

Gly Gly Ala Ala Ser Gln Pro His Arg Ala Ala Thr Phe Leu Pro Leu
            20                  25                  30

Lys Arg Arg Thr Ile Ser Ala Ile His Ala Ala Asp Pro Ser Lys Asn
        35                  40                  45

Asn Gly Pro Ala Val Pro Ala Ala Ala Ala Lys Ser Ser Ala Ser
    50                  55                  60

Ala Val Ala Thr Pro Glu Lys Asn Pro Ala Ala Pro Val Lys Trp Ala
65                  70                  75                  80

Val Asp Ser Trp Lys Ser Lys Lys Ala Leu Gln Leu Pro Glu Tyr Pro
                85                  90                  95

Asn Gln Glu Glu Leu Asp Thr Val Leu Lys Thr Ile Glu Thr Phe Pro
            100                 105                 110

Pro Val Val Phe Ala Gly Glu Ala Arg His Leu Glu Arg Met Ala
        115                 120                 125

Glu Ala Ala Met Gly Arg Ala Phe Ile Leu Gln Gly Gly Asp Cys Ala
    130                 135                 140

Glu Ser Phe Lys Glu Phe His Ala Asn Asn Ile Arg Asp Thr Phe Arg
145                 150                 155                 160

Ile Leu Leu Gln Met Gly Ala Val Leu Met Phe Gly Gly Gln Val Pro
```

-continued

```
               165                 170                 175
Val Val Lys Val Gly Arg Met Ala Gly Gln Phe Ala Lys Pro Arg Ser
            180                 185                 190
Glu Pro Leu Glu Glu Arg Asp Gly Val Lys Leu Pro Ser Tyr Arg Gly
        195                 200                 205
Asp Asn Val Asn Gly Asp Asp Phe Thr Glu Lys Ser Arg Val Pro Asp
    210                 215                 220
Pro Gln Arg Met Ile Arg Ala Tyr Ser Gln Ser Val Ala Thr Leu Asn
225                 230                 235                 240
Leu Leu Arg Ala Leu Ala Thr Gly Gly Tyr Ala Ala Met Gln Arg Val
            245                 250                 255
Thr Gln Trp Asn Leu Asp Phe Met Asp His Ser Glu Gln Gly Asp Arg
        260                 265                 270
Tyr Arg Glu Leu Gly His Arg Val Asp Glu Ala Leu Gly Phe Met Thr
    275                 280                 285
Ala Ala Gly Leu Thr Val Asp His Pro Ile Met Thr Thr Thr Asp Phe
290                 295                 300
Trp Thr Ser His Glu Cys Leu Leu Pro Tyr Glu Gln Ser Leu Thr
305                 310                 315                 320
Arg Lys Asp Ser Thr Ser Gly Leu Phe Tyr Asp Cys Ser Ala His Met
            325                 330                 335
Leu Trp Phe Gly Glu Arg Thr Arg Gln Leu Asp Gly Ala His Val Glu
        340                 345                 350
Ser Leu Arg Gly Val His Asn Pro Leu Gly Ile Lys Val Ser Asp Lys
    355                 360                 365
Met Asn Pro Ser Asp Leu Val Lys Leu Ile Glu Ile Leu Asn Pro Ser
370                 375                 380
Asn Lys Pro Gly Arg Ile Thr Ile Ile Thr Arg Met Gly Ala Glu Asn
385                 390                 395                 400
Met Arg Val Lys Leu Pro His Leu Ile Arg Ala Val Arg Asn Ala Gly
            405                 410                 415
Leu Ile Val Thr Trp Ile Thr Asp Pro Met His Gly Asn Thr Ile Lys
        420                 425                 430
Ala Pro Cys Gly Leu Lys Thr Arg Pro Phe Asp Ser Ile Leu Ala Glu
    435                 440                 445
Val Arg Ala Phe Phe Asp Val His Asp Gln Glu Gly Ser His Pro Gly
    450                 455                 460
Gly Ile His Leu Glu Met Thr Gly Gln Asn Val Thr Glu Cys Ile Gly
465                 470                 475                 480
Gly Ser Arg Thr Val Thr Phe Asp Asp Leu Ser Asp Arg Tyr His Thr
            485                 490                 495
His Cys Asp Pro Arg Leu Asn Ala Ser Gln Ser Leu Glu Leu Ala Phe
        500                 505                 510
Ile Ile Ala Glu Arg Leu Arg Lys Arg Arg Met Arg Ser Gly Leu Asn
    515                 520                 525
Asn Ser Leu Pro Leu Pro Pro Leu Ala Phe
530                 535
```

<210> SEQ ID NO 3
<211> LENGTH: 541
<212> TYPE: DNA
<213> ORGANISM: Oryza sativa

<400> SEQUENCE: 3

```
gatgaccatg atcaagaagg tagccaccca ggaggtatcc acctggaaat gactgggcag    60
aacgtgactg aatgcatcgg tggatcaagg accgtcacct tcgatgacct gagcgaccgc   120
taccacaccc actgtgaccc aaggctgaac gcgtcgcaat ccctggagct cgccttcatc   180
atcgccgaga gactgaggcg gaggaggatg cggtccgggg tcaacagcaa cctgccattg   240
cccccattgg ctttctaaac tgctgaaacg ggggaaggga aaagaaactg ggaggagggg   300
gtagaatagt ttcaactcgc cggcggtgat atctgcatgt gttctgtcaa atgtttgtat   360
ggtggttgtt gagtgttctt ggcactatag gcagttgtcg aggatatggt agcatatata   420
ctcgccgtgt tgtaataagt tttttgatgg atgtgttctg atgaattttt aagggggcct   480
cagctctgtg ctgtttggcc ttggggacag gggaaaataa agctagatgg tttgcttggt   540
t                                                                   541
```

<210> SEQ ID NO 4
<211> LENGTH: 85
<212> TYPE: PRT
<213> ORGANISM: Oryza sativa

<400> SEQUENCE: 4

```
Asp Asp His Asp Gln Glu Gly Ser His Pro Gly Gly Ile His Leu Glu
 1               5                  10                  15

Met Thr Gly Gln Asn Val Thr Glu Cys Ile Gly Gly Ser Arg Thr Val
            20                  25                  30

Thr Phe Asp Asp Leu Ser Asp Arg Tyr His Thr His Cys Asp Pro Arg
        35                  40                  45

Leu Asn Ala Ser Gln Ser Leu Glu Leu Ala Phe Ile Ile Ala Glu Arg
    50                  55                  60

Leu Arg Arg Arg Arg Met Arg Ser Gly Val Asn Ser Asn Leu Pro Leu
65                  70                  75                  80

Pro Pro Leu Ala Phe
            85
```

<210> SEQ ID NO 5
<211> LENGTH: 871
<212> TYPE: DNA
<213> ORGANISM: Oryza sativa
<220> FEATURE:
<221> NAME/KEY: unsure
<222> LOCATION: (575)
<223> OTHER INFORMATION: n = A, C, G, or T

<400> SEQUENCE: 5

```
cgcctaccgc cgccctcacg cctcctccca cctacctcac ctcgaagctg acgtcagcaa    60
tggcgctcgc caccaactcc gccgctgttt ccggtgcgc tgcggccgcg cgtcgtcgg    120 cgccccagcc gcggctcgcc gccacgttcc tcccgatgag gaggcgaacc gtctcggcgg   180
tccacgcggc cgaccggcg aagagcaacg ggcccgtgca ggccgcggcg aaggcctcgt   240
ccccgtcgac ggtggcggcg ccggagaaga agccggtggg gttggggaag tggacggtgg   300
atagctggaa ggcgaagaag gcgctgcagc tgcccgagta cccgagccag gaggagctcg   360
actccgtgct caagacgatc gagacgttcc gcccgtggt gttcgccggg gaggcgcgcc   420
acctcgagga gcgcctcgcc gacgccgcca tgggccgcgc cttcgtcctc cagggcggcg   480
actcgccgga gagcttcaag gagttcaccg ccatcagcat ccgtgacacc ttccgcatcc   540
tgctccagat gggccgcgtc ctcatgttcg gcggncagat gccgtcgtc aaggtcggga   600 ggatggctgg gcagttcgcc aggccgaagt ctgaatcgtt ccaggagaag gacggggtaa   660
```

```
gcttgccagt tacaggggag acaacatcaa tggcgacacc ttccaccaag aagagccgcg    720
tgccggaccc gcagcggatg atccgcgcct accccaatc cgtggcaacg ctcaaactgg     780
tcggggcttc cgcacggaag gtaagcccca tgcagcgcgt cacgcattgg aacctccatt    840
cacgggtaca acgaacagga gacaaggtcc g                                   871
```

<210> SEQ ID NO 6
<211> LENGTH: 270
<212> TYPE: PRT
<213> ORGANISM: Oryza sativa
<400> SEQUENCE: 6

```
Met Ala Leu Ala Thr Asn Ser Ala Ala Val Ser Gly Gly Ala Ala Ala
  1               5                  10                  15

Ala Ala Ser Ser Ala Pro Gln Pro Arg Leu Ala Ala Thr Phe Leu Pro
             20                  25                  30

Met Arg Arg Arg Thr Val Ser Ala Val His Ala Ala Asp Pro Ala Lys
         35                  40                  45

Ser Asn Gly Pro Val Gln Ala Ala Lys Ala Ser Ser Pro Ser Thr
     50                  55                  60

Val Ala Pro Glu Lys Lys Pro Val Gly Leu Gly Lys Trp Thr Val
 65                  70                  75                  80

Asp Ser Trp Lys Ala Lys Lys Ala Leu Gln Leu Pro Glu Tyr Pro Ser
                 85                  90                  95

Gln Glu Glu Leu Asp Ser Val Leu Lys Thr Ile Glu Thr Phe Pro Pro
            100                 105                 110

Val Val Phe Ala Gly Glu Ala Arg His Leu Glu Glu Arg Leu Ala Asp
        115                 120                 125

Ala Ala Met Gly Arg Ala Phe Val Leu Gln Gly Gly Asp Cys Ala Glu
    130                 135                 140

Ser Phe Lys Glu Phe Thr Ala Ile Ser Ile Arg Asp Thr Phe Arg Ile
145                 150                 155                 160

Leu Leu Gln Met Gly Arg Val Leu Met Phe Gly Gly Gln Met Pro Val
                165                 170                 175

Val Lys Val Gly Arg Met Ala Gly Gln Phe Ala Arg Pro Lys Ser Glu
            180                 185                 190

Ser Phe Gln Glu Lys Asp Gly Val Ser Leu Pro Val Thr Gly Glu Thr
        195                 200                 205

Thr Ser Met Ala Thr Pro Ser Thr Lys Lys Ser Arg Val Pro Asp Pro
    210                 215                 220

Gln Arg Met Ile Arg Ala Leu Pro Gln Ser Val Ala Thr Leu Lys Leu
225                 230                 235                 240

Val Gly Ala Ser Ala Arg Lys Val Ser Pro Met Gln Arg Val Thr His
                245                 250                 255

Trp Asn Leu His Ser Arg Val Gln Arg Thr Gly Asp Lys Val
            260                 265                 270
```

<210> SEQ ID NO 7
<211> LENGTH: 1844
<212> TYPE: DNA
<213> ORGANISM: Glycine max
<400> SEQUENCE: 7

```
gcacgagaca aagcccacac accaacttca tttccattca caatgtcaat ttcctccact    60
tccaactccc tcattccccc caaatcttta atccccaat cccaccccct cattcccaac    120
```

-continued

```
atcaggcccg ggctccggcc caagcctggc ccatccccct tccatcctcgc cgtccacgcc      180 gccgagcccg ccaaaaaccc cgtcgtcacc gacaagccca agccccaagc ccaacaatct      240
gcatccccgg ccgcggcccg tgcaaccaaa tgggccgtgg acagctggaa gtccaagaag      300
gccctgcagc tgcccgaata ccccaaccag gaggatctcg aggccgtcct ccgcacccte      360 gacgccttcc ctcccatcgt cttcgccggc gaggcccgga cactcgagga gcacctcgcc      420
gaggccgcca tgggaaatgc cttcctcctc cagggcggag actgtgccga gcttcaag       480 gagttcaatg ccaacaacat ccgtgacacc ttccgcatca tcctccagat gagcgtcgtc      540
atgatgttcg gcggccaaat gcccgtcatc aaggtgggga gaatggcggg gcaatttgcg      600
aagccgaggt cggattcgtt tgaggagaag acggcgtga agcttccgag ttacagaggg      660
gacaacatta acggagactc ctttgacgag aagtcgagga ttccggatcc gcagaggatg      720
attagggctt attgccaagc cgcggcgacg ctgaatcttc tcagagcttt cgccaccggt      780
ggttatgctg ctatgcagag ggttactcag tggaattttgg acttcacgga tcacagcgaa      840
cagggagata ggtaccgaga gcttgctaac cgagttgatg aggctcttgg agtcatggct      900
gctgctgggc tcacagtgga ccatcccata atgagaacaa ctgaattctg acatctcat      960 gagtgcttat tgttgcctta tgaacaatcc ctcaccaggt tggattcaac ttctggtctc     1020
tactatgact gttcagccca tatgctctgg gttggggaac gaaccaggca gcttgatggt     1080
gcccatgtcg agtttctaag aggagttgct aatcccttgg gaattaaggt aagtgacaag     1140
atggatccaa atgagcttgt tagactcatt gagatcttga atcccaaa caaaccaggg      1200 agaataactg tgattacgag gatgggagct gaaaatatga gggtgaagct tccacatctc     1260
atcagggcag tgcgcagagc agggcaaatt gtcacctggg tcagtgatcc tatgcatgga     1320
aacaccatta aggctccatg tggtcttaaa actcgcccct tcgatttcat cagggctgaa     1380
gtgagagcat tctttgatgt gcacgagcaa gaaggaagcc acccaggagg ggttcatcta     1440
gagatgacgg gtcagaatgt gaccgagtgc attggtgggt caaggacggt cacatttgat     1500
gacttgagct cacgttacca cacacactgt gacccaaggc tcaatgcttc acaatctctt     1560
gagcttgctt tcatcatcgc cgagcgtttg agaaagagca ggatcagatc gcagcaacct     1620 cttgccccc taggagtgta aaagtgcctt caaaaccaac aagagaaaga tattttgtt     1680 ctttttttt tttgtcctac atatttatta ttaatcgatg gttgtcactt tgattttgtg     1740
ttgtgtttgt atgtgtatac tacctagtaa tgcgtttgga ctggcaagga caagagtact     1800
tctatggata ataaagaaac gaaaacgttt caattgcgtt ggct                    1844
```

<210> SEQ ID NO 8
<211> LENGTH: 532
<212> TYPE: PRT
<213> ORGANISM: Glycine max

<400> SEQUENCE: 8

```
Met Ser Ile Ser Ser Thr Ser Asn Ser Leu Ile Pro Pro Lys Ser Leu
1               5                  10                  15

Ile Pro Gln Ser His Pro Leu Ile Pro Asn Ile Arg Pro Gly Leu Arg
                20                  25                  30

Pro Lys Pro Gly Pro Ser Pro Ser Ile Leu Ala Val His Ala Ala Glu
            35                  40                  45

Pro Ala Lys Asn Pro Val Val Thr Asp Lys Pro Lys Pro Gln Ala Gln
        50                  55                  60
```

```
Gln Ser Ala Ser Pro Ala Ala Arg Ala Thr Lys Trp Ala Val Asp
 65              70                  75                  80

Ser Trp Lys Ser Lys Lys Ala Leu Gln Leu Pro Glu Tyr Pro Asn Gln
                 85                  90                  95

Glu Asp Leu Glu Ala Val Leu Arg Thr Leu Asp Ala Phe Pro Pro Ile
            100                 105                 110

Val Phe Ala Gly Glu Ala Arg Thr Leu Glu Glu His Leu Ala Glu Ala
            115                 120                 125

Ala Met Gly Asn Ala Phe Leu Leu Gln Gly Gly Asp Cys Ala Glu Ser
130             135                 140

Phe Lys Glu Phe Asn Ala Asn Asn Ile Arg Asp Thr Phe Arg Ile Ile
145             150                 155                 160

Leu Gln Met Ser Val Val Met Met Phe Gly Gly Gln Met Pro Val Ile
                165                 170                 175

Lys Val Gly Arg Met Ala Gly Gln Phe Ala Lys Pro Arg Ser Asp Ser
            180                 185                 190

Phe Glu Glu Lys Asn Gly Val Lys Leu Pro Ser Tyr Arg Gly Asp Asn
            195                 200                 205

Ile Asn Gly Asp Ser Phe Asp Glu Lys Ser Arg Ile Pro Asp Pro Gln
210             215                 220

Arg Met Ile Arg Ala Tyr Cys Gln Ala Ala Thr Leu Asn Leu Leu
225             230                 235                 240

Arg Ala Phe Ala Thr Gly Gly Tyr Ala Ala Met Gln Arg Val Thr Gln
            245                 250                 255

Trp Asn Leu Asp Phe Thr Asp His Ser Glu Gln Gly Asp Arg Tyr Arg
            260                 265                 270

Glu Leu Ala Asn Arg Val Asp Glu Ala Leu Gly Val Met Ala Ala Ala
            275                 280                 285

Gly Leu Thr Val Asp His Pro Ile Met Arg Thr Thr Glu Phe Trp Thr
    290                 295                 300

Ser His Glu Cys Leu Leu Pro Tyr Glu Gln Ser Leu Thr Arg Leu
305             310                 315                 320

Asp Ser Thr Ser Gly Leu Tyr Tyr Asp Cys Ser Ala His Met Leu Trp
            325                 330                 335

Val Gly Glu Arg Thr Arg Gln Leu Asp Gly Ala His Val Glu Phe Leu
            340                 345                 350

Arg Gly Val Ala Asn Pro Leu Gly Ile Lys Val Ser Asp Lys Met Asp
            355                 360                 365

Pro Asn Glu Leu Val Arg Leu Ile Glu Ile Leu Asn Pro Gln Asn Lys
370             375                 380

Pro Gly Arg Ile Thr Val Ile Thr Arg Met Gly Ala Glu Asn Met Arg
385             390                 395                 400

Val Lys Leu Pro His Leu Ile Arg Ala Val Arg Arg Ala Gly Gln Ile
                405                 410                 415

Val Thr Trp Val Ser Asp Pro Met His Gly Asn Thr Ile Lys Ala Pro
                420                 425                 430

Cys Gly Leu Lys Thr Arg Pro Phe Asp Phe Ile Arg Ala Glu Val Arg
            435                 440                 445

Ala Phe Phe Asp Val His Glu Gln Glu Gly Ser His Pro Gly Gly Val
            450                 455                 460

His Leu Glu Met Thr Gly Gln Asn Val Thr Glu Cys Ile Gly Gly Ser
465             470                 475                 480

Arg Thr Val Thr Phe Asp Asp Leu Ser Ser Arg Tyr His Thr His Cys
```

-continued

```
                    485                 490                 495
Asp Pro Arg Leu Asn Ala Ser Gln Ser Leu Glu Leu Ala Phe Ile Ile
            500                 505                 510
Ala Glu Arg Leu Arg Lys Ser Arg Ile Arg Ser Gln Gln Pro Leu Ala
            515                 520                 525
Pro Leu Gly Val
            530
```

<210> SEQ ID NO 9
<211> LENGTH: 1105
<212> TYPE: DNA
<213> ORGANISM: Triticum aestivum

<400> SEQUENCE: 9

```
gcacgaggtg aattggccca tagggtggat gatgctcttg ggttcatgac tgcatcgggg      60
cttacagtcg accaccgat  aatgacgact actgacttct ggacctcgca cgagtgcctt     120
ctcttaccct acgagcaggc tcttacccgt gaggattcca ccagtggcct tttctatgat     180
tgttcggccc acatgttgtg ggttggtgag cgcactcgac aactcgatgg agctcatgtt     240
gaattcctcc gtggtgttgc aaccctctg  ggcataaagg tgagcgacaa aatgaacccc     300
agtgagttgg tgaagctgat tgatattctg aaccettcaa acaaacctgg aaggatcacc     360
ataattacaa ggatgggggc agagaacatg agggtgaagt tgcctcatct catccgtgct     420
gttcgcaatg ctggactgat tgtcacatgg attactgatc ctatgcatgg aaacaccatc     480
aaggcccctt gtgggctgaa gactcgtcca tttgactcca ttctggctga agtgcgtgcc     540
ttcttcgatg tgcatgacca agaaggaagc caccctgggg gcgtccacct tgaaatgact     600
gggcagaatg tgaccgagtg catcggtgga tcacggaccg tgaccttcga cgatctgagc     660
gaccgctacc acaccactg  cgacccaagg ctgaatgcct cccagtccct ggagctcgcc     720
tttatcatcg cagagaggct gaggaagagg aggatgcgat cggggctcaa cagcagcctg     780
ccactgccgc cactggcttt ctgagtagcc ggagccaaac acaaaggagg gtaggaatag     840
ctgtggtgac tcggaagaga aagagacagt cgacgccttg ttttgttgat gcttagtgtg     900
gtgacctggt ggtggtggtg gtgggtgttc ttggcacaag ttacatgctg gggatagcta     960
taggaggtac ctgttgaggt gtgtaagaca gtagctagca accgtatgcc ttggtttcct    1020
gtttgggtgc gtgacttgcc gactttctag ctgcttctgg ggttttgacc tcggtaagga    1080
aagaataaaa agataatcgg agtgc                                         1105
```

<210> SEQ ID NO 10
<211> LENGTH: 267
<212> TYPE: PRT
<213> ORGANISM: Triticum aestivum

<400> SEQUENCE: 10

```
Ala Arg Gly Glu Leu Ala His Arg Val Asp Asp Ala Leu Gly Phe Met
 1               5                  10                  15
Thr Ala Ser Gly Leu Thr Val Asp His Pro Ile Met Thr Thr Thr Asp
                20                  25                  30
Phe Trp Thr Ser His Glu Cys Leu Leu Leu Pro Tyr Glu Gln Ala Leu
            35                  40                  45
Thr Arg Glu Asp Ser Thr Ser Gly Leu Phe Tyr Asp Cys Ser Ala His
        50                  55                  60
Met Leu Trp Val Gly Glu Arg Thr Arg Gln Leu Asp Gly Ala His Val
 65                  70                  75                  80
```

-continued

```
Glu Phe Leu Arg Gly Val Ala Asn Pro Leu Gly Ile Lys Val Ser Asp
                85                  90                  95

Lys Met Asn Pro Ser Glu Leu Val Lys Leu Ile Asp Ile Leu Asn Pro
            100                 105                 110

Ser Asn Lys Pro Gly Arg Ile Thr Ile Ile Thr Arg Met Gly Ala Glu
        115                 120                 125

Asn Met Arg Val Lys Leu Pro His Leu Ile Arg Ala Val Arg Asn Ala
    130                 135                 140

Gly Leu Ile Val Thr Trp Ile Thr Asp Pro Met His Gly Asn Thr Ile
145                 150                 155                 160

Lys Ala Pro Cys Gly Leu Lys Thr Arg Pro Phe Asp Ser Ile Leu Ala
                165                 170                 175

Glu Val Arg Ala Phe Phe Asp Val His Asp Gln Glu Gly Ser His Pro
            180                 185                 190

Gly Gly Val His Leu Glu Met Thr Gly Gln Asn Val Thr Glu Cys Ile
        195                 200                 205

Gly Gly Ser Arg Thr Val Thr Phe Asp Asp Leu Ser Asp Arg Tyr His
    210                 215                 220

Thr His Cys Asp Pro Arg Leu Asn Ala Ser Gln Ser Leu Glu Leu Ala
225                 230                 235                 240

Phe Ile Ile Ala Glu Arg Leu Arg Lys Arg Met Arg Ser Gly Leu
                245                 250                 255

Asn Ser Ser Leu Pro Leu Pro Pro Leu Ala Phe
            260                 265
```

Appendix A

```
              10        20        30        40        50        60
     ---------+---------+---------+---------+---------+---------+
  1  MALSSTSTTNSLLPNRS-LVQNQPLLPSPLKNAFFSNNSTKT--VRFVQPISAVHSSDSN  584777
  1  MALSSSSTTNSLLPNKSQLVQNQSLLPSPLKNVSFTTNSTKP--VRFVQPISAIHSSDSS  114193
  1  MALSNASSA---LVSRSLLPSYKSQSNQPALTFLLPASTTNHLQPKSHHPISAVHAAEPA  2546988
  1  MALTNS--HNTLLPNKALVRHSQPLLP---KTSNFVSNPSKP-SIRSVEPISAVHAADKP  2398679
  1  MALATNSAA----AAAAAVSGGAASQPHRAATFL-------PLKRR---TISAIHAADPS  SEQ ID NO2
  1  MSIS--STSNSLIPPKSLIPQSHPLIPN-IRPGLRPKPGPSP-SI------LAVHAAEPA  SEQ ID NO8
     *                                                  *  *  *
              70        80        90       100       110       120
     ---------+---------+---------+---------+---------+---------+
 58  KIPIVSDKPSKSSPPAATATTAPAPA-VTKTEWAVDSWKSKKALQLPEYPNQEELRSVLK  584777
 59  KNPIVSDKPSSKPSPPAATVTAAATT-VTKTEWTVESWKSKKALQKPEYPNQEELQSVLK  114193
 58  KTPI-----TSTTAAAASTKAAPSVE-GKOGKWSLESWKKKKALOLPEYPNEEELOAVLR  2546988
 55  QKPTP---PSATVSSAVPTVSAPVVK-IPEKKWTLESWKTKKALQLPEYPDQVELESVLK  2398679
 47  KNNGPAVPAAAAAKKSSASAVATPEKNPAAPVKWAVDSWKSKKALQLPEYPNEELDTVLK  SEQ ID NO2
 51  KNPVVTDKPKPQAQQSPSPAAARA------TKWAVDSWKSKKALQLPEYPQEDLEAVLR  SEQ ID NO8
                                       *  *** **********   *  **
             130       140       150       160       170       180
     ---------+---------+---------+---------+---------+---------+
117  TIDEFPPIVFAGEARSLEERLGEAAMGRAFLLQGGDCAESFKEFNANNIRDTFRILLQMG  ST584777
118  TIEEFPPIVFAGEARSLEERLGEAAMGRAFLLQGGDCAESFKEFNANNIRDTFRILLQMG  NT114193
112  TIEAYPPLVFAGEARNLEERIAQAAMGNAFLLQGGDCAESFKEFNANNIRDTFRILLQMS  MC2546988
111  TLDSFPPIVFAGEARSLEERLAEAAMGNAFLLQGGDCAESFKEFNANNIRDTFRILLQMG  MC2398679
107  TIETFPPVVFAGEARHLEERMAEAAMGRAFILQGGDCAESFKEFNANNIRDTFRILLQMG  SEQ ID NO2
105  TLDAFPPIVFAGEARTLEEHLAEAAMGNAFLLQGGDCAESFKEFNANNIRDTFRIILQMS  SEQ ID NO8
     *  ** ******  ***    **** ** *************  **********  ***
```

Appendix A-continued

```
              190       200       210       220       230       240
     ---------+---------+---------+---------+---------+---------+
177  AVLMFGGQMPVIKVGRMAGQFAKPRSDSFEEKDGVKLPSYRGDNVNGDAFDVKSRTPDPQ  ST584777
178  AVLMFGGQMPVIKVGRMAGQFAKPRSDNFEEKNGVKLPSYRGDNVNGDAFDAKSRTPDPQ  NT114193
172  VVLMFGGQMPVVKVGRMAGQFAKPRSDPFEEKDGVKLPSYKGDNINGDTFDEKSRLPDPQ  MC2546988
171  AVLMFGGQMPVIKVGRMAGQFAKPRSEPFEEKNGVKLPSYRGDNVNGDAFDAKSRAPDPQ  MC2398679
167  AVLMFGGQVPVVKVGRMAGQFAKPRSEPLEERDGVKLPSYRGDNVNGDDFTEKSRVPDPQ  SEQ ID NO2
165  VVMMFGGQMPVIKVGRMAGQFAKPRSDSFEEKNGVKLPSYRGDNINGDSFDEKSRIPDPQ  SEQ ID NO8
     * ***** ** **************  **  ***********  *** *  *** ****

250       260       270       280       290       300
     ---------+---------+---------+---------+---------+---------+
237  RLIRAYCQSAATLNLLRAFATGGYAAMQRINQWNLDFTEHSEQGDRYRELASRVDEALGF  ST584777
238  RLIRAYCQSAATLNLLRAFATGGYAAMQRINQWNLDFTEHSEQGDRYRELANRVDEALGF  NT114193
232  RLIRAYCQSAATLNLLRAFATGGYAAMQRVTEWNLDFVEHSEQGDRYQELAHRVDEALGF  MC2546988
231  RMIRAYCQAAATLNLLRAFATGGYAAMQRVTQWNLDFTEHSEQGDRYRELAHRVDEALGF  MC2398679
227  RMIRAYSQSVATLNLLRALATGGYAAMQRVTQWNLDFMDHSEQGDRYRELGHRVDEALGF  SEQ ID NO2
225  RMIRAYCQAAATLNLLRAFATGGYAAMQRVTQWNLDFTDHSEQGDRYRELANRVDEALGV  SEQ ID NO8
     * *** * ******** **********    *****  ********  **  *******

310       320       330       340       350       360
     ---------+---------+---------+---------+-----    +---  ----  --+
297  MTAAGLTMDHPIMKTTEFWTSHECLLLPYEQSLTRRDSTSGLYYD CSAH FLWV GERT RQL  ST584777
298  MAAAGLTVDHPIMKTTEFWTSHECLLLPYEQSLTRLDSTSGLYYD CSAH FIWV GERT RQL  NT114193
292  MAAAGLTIDHPIMSSTEFWTSHECLLLPYEQALSREDSTSGLFYD CSAH MLWV GERT RQL  MC2546988
291  MSAAGLTMDHPIMTTTEFWTSHECLLLPYEQSLTRLDSTSGLYYD CSAH FLWV GERT RQL  MC2398679
287  MTAAGLTVDHPIMTTTDFWTSHECLLLPYEQSLTRKDSTSGLFYD CSAH MLWF GERT RQL  SEQ ID NO2
285  MAAAGLTVDHPIMRTTEFWTSHECLLLPYEQSLTRLDSTSGLYYD CSAH MLWV GERT RQL  SEQ ID NO8
     * ***** *****  * **************  *  ******  ** ****   *  **** ***

370       380       390       400       410       420
     ---------+---------+---------+---------+---------+---------+
357  DGAHVEFLRGIANPLGIKVSDKMDPSALVKLIEILNPQNKAGRITIITRMGAENMRVKLP  ST584777
358  DGAHVEFLRGVANPLGIKVSDKMDPSALVKLIEILNPDNKAGRITIITRMGAENMRVKLP  NT114193
352  DGAHVEFLRGVSNPLGIKVSQKMDPKELVNIIEILNPTNKPGRITVIVRMGAENMRVKLP  MC2546988
351  DGAHVEFLRGVANPLGIKVSDKMDPNELVKLIEILNPQNKAGRITIITRMGAENMRVKLP  MC2398679
347  DGAHVESLRGVHNPLGIKVSDKMNPSDLVKLIEILNPSNKPGRITIITRMGAENMRVKLP  SEQ ID NO2
345  DGAHVEFLRGVANPLGIKVSDKMDPNELVRLIEILNPQNKPGRITVITRMGAENMRVKLP  SEQ ID NO8
     ****** *** ********  ** *  ** ******* ** ****  ************

430       440       450       460       470       480
     ---------+---------+---------+---------+---------+---------+
417  HLIRAVRRAGQIVTWVSDPMHGNTIKAPCGLKTRPFDSIRAEVRAFFDVHDQEGSHPGGV  ST584777
418  HLIRAVRRAGQIVTWVSDPMHGNTIKAPCGLKTRPFDSIRAEVRAFFDVHEQEGSHPGGV  NT114193
412  HLIRAVRGAGQIVTWVCDPMHGNTIKAPCGLKTRAFDAILAEVRGFFDVHEQEGSHPGGV  MC2546988
411  HLIRAVRRAGQIVTWVSDPMHGNTIKAPCGLKTRPFDAIRAEVRAFFDVHEQEGSHPGGV  MC2398679
407  HLIRAVRNAGLIVTWITDPMHGNTIKAPCGLKTRPFDSILAEVRAFFDVHEQEGSHPGGI  SEQ ID NO2
405  HLIRAVRRAGQIVTWVSDPMHGNTIKAPCGLKTRPFDFIRAEVRAFFDVHEQEGSHPGGV  SEQ ID NO8
     ******* ** ***** ****************  ** * **** ***** ********

490       500       510       520       530       540
     ---------+- _ -------+---------+---------+---------+---------+
477  HLEMTGQNVTE C IGGSRTVTFDDLSSRYHTHCDPRLNASQSLELSFIIAERLRKRR----  ST584777
478  HLEMTGQNVTE C IGGSRTVTFDDLSSRYHTHCDPRLNASQSLELAFIIAERLRKRR----  NT114193
472  HLEMTGQNVTE C IGGSRTVTYDDLSSRYHTHCDPRLNASQSLELAFIIAERLRKRR----  MC2546988
471  HLEMTGQNVTE C IGGSRTVTFDDLGSRYHTHCDPRLNASQSLELAFIIAERLRKRR----  MC2398679
467  HLEMTGQNVTE C IGGSRTVTFDDLSDRYHTHCDPRLNASQSLELAFIIAERLRKRRMRSG  SEQ ID NO2
465  HLEMTGQNVTE C IGGSRTVTFDDLSSRYHTHCDPRLNASQSLELAFIIAERLRKSR----  SEQ ID NO8
     *********** * ******** ***  ******************** ********* *

550
     ---------+--
533  LGSQSV               ST584777
534  LGSQNVL---GQ         NT114193
528  MGSQRP----AF         MC2546988
527  LGSPKSL---AY         MC2398679
527  LNNSLPLPPLAF         SEQ ID NO2
521  IRSQQPLAPLGV         SEQ ID NO8
```

What is claimed is:

1. An isolated polynucleotide comprising:
   (a) a nucleotide sequence encoding a polypeptide having DAHP synthetase activity, wherein the polypeptide has an amino acid sequence of at least 90% sequence identity, based on the Clustal method of alignment, when compared to SEQ ID NO:8; or
   (b) a full complement of the nucleotide sequence of (a).

2. The isolated polynucleotide of claim 1, wherein the polypeptide has an amino acid sequence comprising SEQ ID NO:8.

3. The isolated polynucleotide of claim 1, wherein nucleotide sequence comprises SEQ ID NO:7.

4. A recombinant DNA construct comprising the isolated polynucleotide of claim 1 operably linked to at least one regulatory sequence.

5. A transformed host cell comprising the recombinant DNA construct of claim 4.

6. A vector comprising the isolated polynucleotide of claim 1.

7. A method for isolating a polypeptide having DAHP synthetase activity comprising isolating the polypeptide from a cell or culture medium of the cell, wherein the cell comprises the recombinant DNA construct of claim 4.

* * * * *

UNITED STATES PATENT AND TRADEMARK OFFICE
CERTIFICATE OF CORRECTION

PATENT NO. : 6,911,331 B2
DATED : June 28, 2005
INVENTOR(S) : Famodu Omolayo O., Hitz William D. and Lightner Jonathan E.

It is certified that error appears in the above-identified patent and that said Letters Patent is hereby corrected as shown below:

Title page,
Item [60], Related U.S. Application Data, delete "Provisional application No. PCT/US99/16352, filed on Jul. 20, 1999, and provisional application No. 60/093,611, filed on Jul. 21, 1998" and insert therefor -- National Stage of International Application No. PCT/US99/16352, filed July 20, 1999, which claims benefit of U.S. Provisional Appln. No. 60/093,611, filed July 21, 1998. --.
Item [56], References Cited, OTHER PUBLICATIONS,
"Klaus M. Herrmann" reference, after "107:" insert therefor -- 7-12, --;
"Gary Millar" reference, after "200(1):" insert therefor -- 11-17, --.

Signed and Sealed this

Twenty-ninth Day of November, 2005

JON W. DUDAS
*Director of the United States Patent and Trademark Office*